(12) United States Patent
Fleckenstein et al.

(10) Patent No.: US 6,218,140 B1
(45) Date of Patent: *Apr. 17, 2001

(54) ENHANCER FOR EUKARYOTIC EXPRESSION SYSTEMS

(75) Inventors: Bernhard Fleckenstein, Schlaifhausen (DE); Walter Schaffner, Weiningen (CH); Frank Weber, Rheinfelden (CH); Karoline Dorsch-Häsler, Zürich (CH); Gerhard Jahn, Neunkirchen (DE); Michael Boshart, Heidelberg (DE)

(73) Assignee: Hoechst Aktiengesellschaft, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 08/338,213

(22) Filed: Nov. 9, 1994

Related U.S. Application Data

(63) Continuation of application No. 07/285,330, filed on Dec. 14, 1988, now abandoned, which is a continuation of application No. 07/170,140, filed on Mar. 14, 1988, now abandoned, which is a continuation of application No. 07/059,228, filed on Jun. 4, 1987, now abandoned, which is a continuation of application No. 06/768,816, filed on Aug. 23, 1985, now abandoned.

(30) Foreign Application Priority Data

Aug. 24, 1984 (DE) ................................ 34 31 140

(51) Int. Cl.⁷ ........................ C12P 21/00; C12N 15/85; C12N 15/63; C07H 21/04
(52) U.S. Cl. ........................ 435/69.1; 435/455; 435/456; 435/320.1; 435/325; 435/91.4; 435/91.41; 536/23.1; 536/24.1
(58) Field of Search ............................ 435/69.1, 172.1, 435/172.3, 320.1, 240.2, 455, 456, 325, 91.4, 91.41; 536/23.1, 24.1

(56) References Cited

U.S. PATENT DOCUMENTS

| | | | |
|---|---|---|---|
| 5,168,062 | * 12/1992 | Stinski | 435/240.2 |
| 5,385,839 | 1/1995 | Stinski | 435/366 |
| 5,849,522 | * 12/1998 | Flechenstein et al. | 435/69.1 |

OTHER PUBLICATIONS

Weber et al. *Cell* 36:983–992, 1984 (Apr.).*
John et al. *J. Virology* 49(2):363–370, 1984 (Feb.).*
Edlund et al. *Science* 230:912–916, 1985.*
Boulet et al. *Proc. Natl. Acad. Sci.* (USA) 83:3599–3603, 1986.*
Okzki et al. *EMBO, J.* 4:2589–2595, 1985.*
Theiser et al. *EMBO, J.* 5:719–724, 1986.*
Garabedian et al. *Cell* 45:859–867, 1986.*
Ciliberto et al. *Cell* 41:531–540, 1985.*
Gillies et al. *Cell* 33:717–728, 1983.*
Boneji et al *Cell* 33:729–740, 1983.*
Thomsen et al. *P.N.A.S.* 81:659–663, 1984 (Feb.).*
Greenaway et al., "Human cytomegalovirus DNA: BamHI, EcoRI and PstI restriction endonuclease cleavage maps," Gene, 18:355–360 (1982).
Stinski et al., "Organization and Expression of the Immediate Early Genes of Human Cytomegalovirus," J. Virol., 46:1–4 (Apr. 1983).
Stenberg et al., "Structural Analysis of the Major Immediate Early Gene of Human Cytomegalovirus," J. Virol., 49:190–199 (Jan. 1984).
Clanton et al., "Neoplastic transformation by a cloned human cytomegalovirus DNA fragment uniquely homologous to one of the transforming regions of herpes simplex virus type 2," PNAS–USA, 80:3826–3830 (1983).
Nelson et al., "Structure of the Transforming Region of Human Cytomegalovirus AD169," J. Virol., 49:109–115 (Jan. 1984).
Gorman et al., "Recombinant Genomes Which Express Chloramphenicol Acetyl–transferase in Mammalian Cells," Mol. Cell. Biol., 2:1044–1051 (1982).
Laimins et al., "Host–specific activation of transcription by tandem repeats from simian virus 40 and Moloney murine sarcoma virus," PNAS–USA, 79:6453–6457 (1982).
Kaufman et al., "Construction of a Modular Dihydrofolate Reductase cDNA Gene: Analysis of Signals Utilized for Efficient Expression," Mol. Cell. Biol., 2:1304–1319 (1982).
Dynan et al., "Isolation of Transcription Factors That Discriminate between Different Promoters Recognized by RNA Polymerase II," Cell, 32:669–680 (1983).
Breathnach et al., "Plasmids for the cloning and expression of full–length double–stranded cDNAs under control of the SV40 early or late gene promoter," Nucl. Acids Res., 11:7119–7136 (1983).
Kaufman et al., "Growth–Dependent Expression of Dihydrofolate Reductase mRNA from Modular cDNA Gene," Mol. Cell. Biol., 3:1598–1608 (1983).

* cited by examiner

*Primary Examiner*—David Guzo
(74) *Attorney, Agent, or Firm*—Finnegan, Henderson, Farabow, Garrett and Dunner, L.L.P.

(57) ABSTRACT

An enhancer has been located in the upstream region of the major immediate early gene of human cytomegalovirus and has been isolated, which enhancer is more active than that from SV40 and has a wide host cell spectrum. Hence, it is suitable for eukaryotic expression systems wherein it can be incorporated upstream or downstream of the structural gene or of the regulation region.

45 Claims, 2 Drawing Sheets

FIG. 1b

Figure 1A:
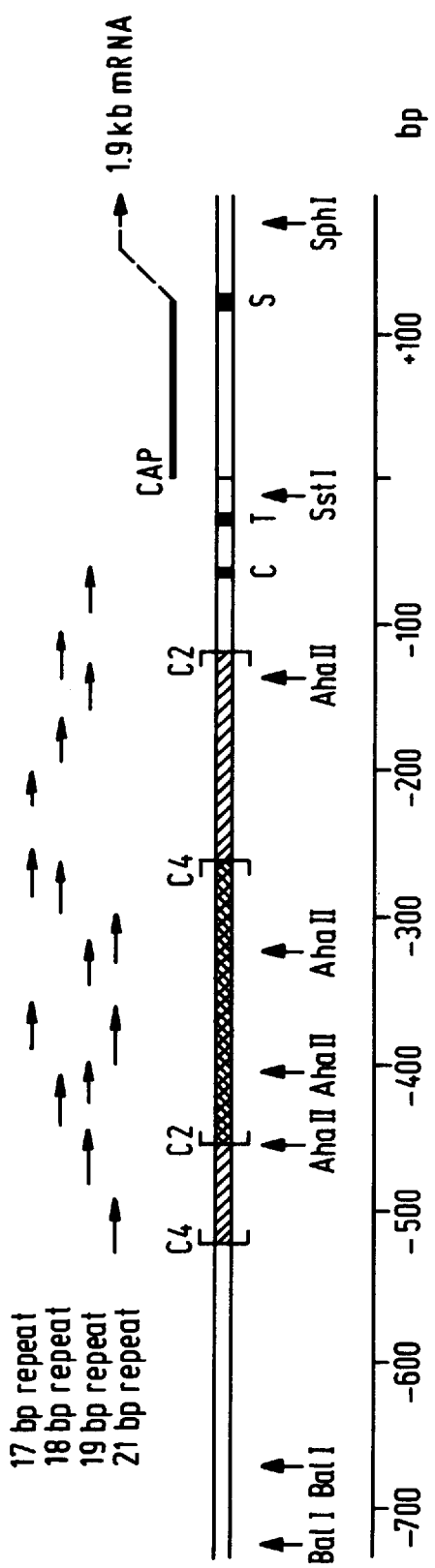

```
-737 AATCAAATATT GGCCATTAGC CATATATATTC ATTGGTTATA TAGCATAAAT CAATATTGGC TATTGGCCAT TGCATACGTT GTATCCATAT CATAAATATGT
             BalI
-637 ACATTTATAT TGGCTCATGT CCAACACATAC CGCCATGTTG ACATTGATTA TTGACTAGTT ATTAAATAGTA ATCAATTACG GGGTCATTAG TTCATAGCCC
-537 ATATATGGAG TTCCGGCGTA CATAAACTTAC GGTAAATGGC CCGCCTGTCT GACCGCCCAA CGACCCCCGC CCATTGACGT CAATAAATGAC GTATGTTCCC
                            C4                         
-437 ATAGTAACGC CAATAGGGAC TTTCCATTGA CGTCAATGGG TGGAGTATTT ACGGTAAACT GCCCACTTGG CAGTACACATCA AGTGTATCAT ATGCCAAGTA
-337 CGCCCCCTAT TGACGTCAAT GACGGTAAAT GGCCCGCCTG GCATTATGCC CAGTACATGA CCTTATGGGA CTTTGCTACT TGGCAGTACA TCTACGTATT
                                                                                   C4
-237 AGTCATCGCT ATTACCATGG TGATGCGGTT TTGGCAGTAC ATCAATGGGC GTGGATAGCG GTTTGACTCA CGGGGATTTC CAAGTCTCCA CCCCATTGAC
-137 GTCAATGGGA GTTTGTTTTG GCACCAAAAT CAACGGGACT TTCCAAAATG TCGTAACAAC TCCGCCCCAT TGACGCAAAT GGGCGGTAGG CGTGTACGGT
                  C2
-37  GGGAGGTCTA TATAAGCAGA GCTCGTTTAG TGAACCGTCA GATCGCCTGG AGACGCCATC CACGCTGTTT TGACCTCCAT AGAAGACACC GGGACCGATC
                          SstI                      +1
+64  CAGCCTCCGC GGCCGGGAAC GGTGCATTGG AACGCGGATT CCCCGTGCCA AGAGTGACGT AAGTACCGCC TATAGAGTCT ATAGGCCCAC CCCCTTGGCT
+164 TCTTATGCAT GCTATACTGT TTTGGCTTG
           SphI
```

ENHANCER FOR EUKARYOTIC EXPRESSION SYSTEMS

This application is a continuation application Ser. No. 07/285,330 filed Dec. 14, 1988, abandoned which is a continuation application of prior application Ser. No. 07/170,140, filed Mar. 14, 1988 (abandoned), which is a continuation application of prior application Ser. No. 07/059,228, filed Jun. 4, 1987 (abandoned), which is a continuation application of prior application Ser. No. 06/768,816, filed Aug. 23, 1985 (abandoned).

The invention is directed to an enhancer for eukaryotic expression systems, containing DNA from the upstream region of the major immediate early (IE) region of human cytomegalovirus (HCMV). According to certain embodiments, the enhancer is obtainable by sonication of the DNA from the IE region of HCMV with the formation of about 300 bp fragments, co-transfection of CV1 monkey cells and enhancerless SV40 genome, isolation of the recombinants which show lytic growth, and isolation of the inserted HCMV DNA, and enhancer-active mutants of this DNA. A process for improvement of eukaryotic expression systems by incorporating the enhancer upstream or downstream of the structural gene or of the regulation region is also provided. According to certain embodiments, the enhancer is incorporated not more than about 7,000 bp, or about 3,000 bp, upstream or downstream of the sites specified. Other advantageous embodiments follow.

The "enhancer trap" is described in F. Weber et al., Cell 36 (1984) 983–992; is respect of HCMV DNA, see G. Jahn et al., J. Virology, Feb. 1984, Vol. 49, 363–370 and literature quoted there, also D. R. Thomsen et al., Proc. Natl. Acad. Sci. USA, 81 (1984), 659–663, and P. J. Greenaway et al., Gene 18 (1982) 355–360.

In the HCMV DNA, the enhancer is located in the Hind III E fragment (Greenaway et al., loc. cit.), which includes the Pst I m fragment (about 2.1 kb).

Two recombinants were isolated by sonication of the DNA from the IE region of HCMV with the formation of about 300 bp fragments, co-transfection of CV1 monkey cells and enhancerless SV40 genome, isolation of the recombinants which show lytic growth, and isolation of the inserted HCMV DNA, and enhancer-active mutants of this DNA. Those recombinants contained 341 and 262 bp of HCMV DNA, located at positions −118 to −458 and −263 to −524 respectively on the published DNA sequence (Greenaway et al., loc. cit.). The overlap of 196 bp contains an essential part of the enhancer. Deletion mutants, for example obtained by Aha II and religation of the fragments in various combinations, are likewise enhancer-active.

The invention also relates to DNA which is a sequence homolog of reisolated HCMV specific enhancer DNA to the extent of at least 75, preferably at least 80, %, or is hybridized therewith.

The enhancer increases the expression of rabbit beta-globin in HeLa cells, after incorporation downstream of the appropriate gene, by at least two orders of magnitude, irrespective of the orientation. Thus the enhancer is superior to that of SV40 by the factor 3 to 5, dependent on the host system.

The HCMV enhancer has activity in a broad spectrum of host cells (cells of primates, mice, rats and frogs). It stimulates the expression of proteins in eukaryotic systems and thus facilitates the production of modified proteins, for example glycoproteins.

It is also possible to eliminate the promoter instrinsic to HCMV, for example by deletion of about 100 bp using Bal 31 beyond the Sac I restriction site. Where appropriate, the enhancer sequence can be modified by the attachment of adaptors of linkers.

When used with the intrinsic promoter, it is possible for a eukaryotic promoter to be substituted, for example by incorporation with inclusion of the first splice donor consensus sequence of the IE gene before the splice acceptor sequence of the gene which is to be expressed.

The invention is illustrated in detail in the Example which follows.

EXAMPLE

An "enhancer trap" was prepared, by the method of Weber et al., loc. cit., by removal of the 72 bp repeat region (restriction with XbaI and KpnI) from the SV40 genome. The PstI m fragment (2.1 kb) from HCMV, strain AD 169, was broken down by sonication into fragments about 300 bp in size, and co-transfection with the "enhancer trap" was carried out. The recombinant DNA was isolated from the colonies which showed the best lytic growth. By sequencing, a 262 bp segment of HCMV DNA was found in which an end-on-end ligation had occurred on one side, whereas on the other side recombination took place via a 6 bp hemology between HCMV (nucleotides −531 to −526, FIG. 1a) and SV40 (nucleotides 67 to 72). This resulted in a deletion of 27 bp of the SV40 DNA (nucleotides 73 to 99), which affected both 21 bp repeats of the SV40 early promoter. The 262 bp segment is identified in the restriction map (FIG. 1a) and in the DNA sequence (FIG. 1b) by square brackets labeled "C4".

Another enhancer-active recombinant with 341 bp of HCMV DNA proved to be a ligation product having the ends of a linear "enhancer trap" molecule (in which a few bases had been eliminated from the KpnI and XbaI ends of the SV40 DNA, presumably by exonucleolytic deletion before ligation within the transfected cell). The HCMV DNA of this recombinant is identified in FIGS. 1a and 1b by "C2"; it extends from −188 to −458. Thus the segments C2 and C4 overlap over a region of 196 bp.

The Hind III C fragment of the recombinant virus with the C4 insert, and the PstI m fragment of HCMV were first cloned in pUC 8 (J. Vieira et al., Gene 19 (1982) 259–268) in both orientations, excized as Hind III-SalI fragments, and recloned between the HindIII and XhoI restriction site of p βx14, that is to say downstream of the rabbit β-globin gene (J. Banerji et al., Cell 27 (1981) 299–308; J. de Villiers et al., Nucl. Acids Res. 9 (1981) 6251–6254; S. Rusconi et al., Proc. Natl., Acad. Sci. USA 78 (1981) 5051–5055; H. Weber et al., ICN-UCLA Symp. Mol. Cell. Biol. 33 (1981) 367; B. Wasylyk et al., Cell 32 (1983) 503–514). The enhancer action on β-globin transcription was determined by S1 nuclease analysis of cytoplasmic RNA after transient expression in Hela cells.

All recombinants were compared under standardized conditions with analogous recombinants having the SV40 enhancer. It emerged that the HCMV enhancer increases the synthesis of β-globin by at least 2 order of magnitude—irrespective of the orientation.

We claim:

1. An isolated enhancer for animal or mammalian host cell expression systems, consisting of (a) a DNA molecule from position −458 to −118 or position −524 to −263 of the upstream region of the major immediate early (IE) gene of human cytomegolovirus (HCMV) strain AD 169 or (b) a DNA molecule that is at least 80% homologous to the DNA molecule of (a), wherein said DNA molecule of (a) or (b)

enhances the transcription of DNA in an animal or mammalian host cell expression system.

2. An isolated enhancer as claimed in claim 1, obtained by sonication of the DNA from the IE region of HCMV with the formation of about 300 bp fragments, co-transfection of CV1 monkey cells and enhancerless SV40 genome, isolation of the recombinants which show lytic growth, and isolation of the inserted HCMV DNA.

3. A process for improvement of animal or mammalian host cell expression systems, which comprises incorporation of an enhancer as claimed in claim 1, upstream of a regulation region of a structural gene.

4. The process as claimed in claim 3, wherein the enhancer in incorporated not more than about 7,000 bp upstream of the regulation region.

5. The process as claimed in claim 4, wherein the enhancer is incorporated less than 3,000 bp upstream of the regulation region.

6. A process for improvement of animal or mammalian host cell expression systems, which comprises incorporation of an enhancer as claimed in claim 1, downstream of a structural gene.

7. The process as claimed in claim 6, wherein the enhancer is incorporated not more than about 7,000 bp downstream of the structural gene.

8. The process as claimed in claim 7, wherein the enhancer is incorporated less than 3,000 bp downstream of the structural gene.

9. A process for improvement of animal or mammalian host cell expression systems, which comprises incorporation of an enhancer as claimed in claim 1, downstream of a regulation region of a structural gene.

10. The process as claimed in claim 9, wherein the enhancer is incorporated not more than about 7,000 bp downstream of the structural gene.

11. The process claimed in claim 10, wherein the enhancer is incorporated less than 3,000 bp downstream of the structural gene.

12. An isolated enhancer consisting of a nucleotide sequence from position −458 to −118 or position −524 to −263 of the upstream region of the major immediate early (IE) gene of human cytomegalovirus (HCMV) strain AD 169, wherein said enhancer enhances the transcription of DNA in an animal or mammalian host cell expression system.

13. An isolated enhancer as claimed in claim 12, obtained by sonication of the DNA from the IE region of HCMV with the formation of about 300 bp fragments, co-transfection of CV1 monkey cells and enhancerless SV40 genome, isolation of the recombinants which show lytic growth, and isolation of the inserted HCMV DNA.

14. A process for improvement of animal or mammalian host cell expression systems, which comprises incorporation of an enhancer as claimed in claim 12, upstream of a structural gene.

15. The process as claimed in claim 14, wherein the enhancer is incorporated not more than about 7,000 bp upstream of the structural gene.

16. The process as claimed in claim 15, wherein the enhancer is incorporated less than 3,000 bp upstream of the structural gene.

17. A process for improvement of animal or mammalian host cell expression systems, which comprises incorporation of an enhancer as claimed in claim 12, upstream of a regulation region of a structural gene.

18. The process as claimed in claim 17, wherein the enhancer is incorporated not more than about 7,000 bp upstream of the regulation region.

19. The process as claimed in claim 18, wherein the enhancer is incorporated less than 3,000 bp upstream of the regulation region.

20. A process for improvement of animal or mammalian host cell expression systems, which comprises incorporation of an enhancer as claimed in claim 12, downstream of a structural gene.

21. The process as claimed in claim 20, wherein the enhancer is incorporated not more than 7,000 bp downstream of the structural gene.

22. The process as claimed in claim 21, wherein the enhancer is incorporated less than 3,000 bp downstream of the structural gene.

23. A process for improvement of animal or mammalian host cell expression systems, which comprises incorporation of an enhancer as claimed in claim 12, downstream of a regulation region of a structural gene.

24. The process as claimed in claim 23, wherein the enhancer is incorporated not more than about 7,000 bp downstream of the regulation region.

25. The process claimed in claim 24, wherein the enhancer is incorporated less than 3,000 bp downstream of the regulation region.

26. A plasmid comprising an enhancer as claimed in claim 12 and a DNA molecule from the promoter region of a eukaryotic structural gene.

27. A plasmid according to claim 26, further comprising a structural gene.

28. A plasmid according to claim 27, wherein the enhancer is upstream of the structural gene.

29. A plasmid according to claim 27, wherein the enhancer is incorporated not more than about 7,000 bp upstream of the structural gene.

30. A plasmid according to claim 27, wherein the enhancer is incorporated not more than about 3,000 bp upstream of the structural gene.

31. A plasmid according to claim 27, wherein the enhancer is incorporated upstream of a regulation region of the structural gene.

32. A plasmid according to claim 31, wherein the enhancer is incorporated not more than about 7,000 bp upstream of a regulation region of a structural gene.

33. A plasmid according to claim 32, wherein the enhancer is incorporated less than 3,000 bp upstream of a regulation region of the structural gene.

34. A plasmid according to claim 27, wherein the enhancer is downstream of the structural gene.

35. A plasmid according to claim 34, wherein the enhancer is not more than about 7,000 bp downstream of the structural gene.

36. A plasmid according to claim 35, wherein the enhancer is incorporated less than 3,000 bp downstream of the structural gene.

37. A plasmid according to claim 27, wherein the enhancer is downstream of a regulation region of the structural gene.

38. A plasmid according to claim 37, wherein the enhancer is not more than about 7,000 bp downstream of a regulation region of a structural gene.

39. A plasmid according to claim 38, wherein the enhancer is less than 3,000 bp downstream of a regulation region of a structural gene.

40. A plasmid comprising an enhancer as claimed in claim 12 and a heterologous DNA operatively linked to said enhancer.

41. A process for improvement of host cell expression, comprising incorporating a plasmid according to claim 40 into an animal or mammalian host cell.

42. A recombinant DNA plasmid comprising a DNA molecule isolated from the immediate early (IE) promoter/regulatory region of human cytomegalovirus (HCMV) and a heterologous gene positioned downstream and operatively linked to said molecule, wherein the DNA molecule enhances the transcription of DNA in an animal or mammalian host cell expression system.

43. A eukaryotic host cell transformed with a recombinant DNA plasmid comprising a DNA molecule isolated from the immediate early (IE) promoter/regulatory region of human cytomegalovirus (HCMV) and a heterologous gene positioned downstream and operatively linked to said DNA molecule, wherein the DNA molecule enhances the transcription of DNA in an animal or mammalian host cell expression system.

44. The transformed eukaryotic host cell of claim 43 wherein said host cell is a mammalian host cell.

45. A recombinant DNA plasmid comprising a DNA molecule isolated from the PstI m fragment of the immediate early (IE) region of human cytomegalovirus (HCMV) and a heterologous gene positioned downstream and operatively linked to said DNA molecule, wherein said DNA molecule enhances expression of said heterologous gene.

* * * * *

UNITED STATES PATENT AND TRADEMARK OFFICE
CERTIFICATE OF CORRECTION

PATENT NO. : 6,218,140 B1
DATED : April 17, 2001
INVENTOR(S) : Bernhard Fleckenstein et al.

It is certified that error appears in the above-identified patent and that said Letters Patent is hereby corrected as shown below:

Column 3,
Line 13, "in incorporated" should read -- is incorporated --.

Column 4,
Line 9, "not more than 7,000" should read -- not more than about 7,000 --.

Signed and Sealed this

Fifteenth Day of October, 2002

Attest:

Attesting Officer

JAMES E. ROGAN
Director of the United States Patent and Trademark Office